United States Patent [19]

Moore

[11] Plant 4,160

[45] Nov. 29, 1977

[54] MINIATURE ROSE PLANT

[76] Inventor: Ralph S. Moore, 2519 E. Noble Ave., Visalia, Calif. 93277

[21] Appl. No.: 762,029

[22] Filed: Jan. 24, 1977

[51] Int. Cl.[2] ..... A01H 5/00

[52] U.S. Cl. ..... Plt./9

[58] Field of Search ..... Plt./7, 9–10

*Primary Examiner*—Robert E. Bagwill

[57] ABSTRACT

A novel miniature rose variety characterized by its coral pink to light red blossoms.

1 Drawing Figure

1

The present invention relates to a new and distinct variety of hardy, dwarf, bush type rose plant of the miniature class; the variety being primarily characterized — as to novelty — by bright coral pink to light red buds and flowers which in general color effect are similar to Persian Princess (miniature — U.S. Plant Pat. No. 3,161).

The variety is further characterized by:

An abundance of bloom with flowers borne singly or several to stem in loose clusters.

Little or no fragrance.

A plant which is vigorous, of rounded upright shape and with glossy, medium — small foliage with pointed leaflets; the buds and flowers being similar in form and size to Persian Princess.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Fire King (Floribunda — U.S. Plant Pat. No. 1,758) as the seed parent and Little Buckaroo (miniature — U.S. Plant Pat. No. 1,726) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers. Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf; bushy; seedling; greenhouse; outdoors; cut flowers; garden decoration; potted plant.

Class: Miniature. Variety name 'Swedish Doll'.

Flowers:

*Continuity.*—Continuous — repeat bloom all season.

*Fragrance.*—Little or none.

Flowers borne: Singly and several together (3 to 5) on sturdy, wirey, medium length stems.

2

Quantity of bloom: Abundant both outside and in greenhouse.

Bud:

*Penduncle.*—Medium length; slender but sturdy; erect; medium green, sometimes tinted bronze (outdoors); hairs — few or none.

*Before calyx breaks.*—Size — small. Form: medium long; pointed with few foliaceous appendages and few or no hairs on surface of bud; with foliaceous parts extending beyond the tip of the bud equal to one-half or less of its length. Color — medium green, occasionally tinted with bronze (outdoors).

*As calyx breaks.*—Color — light to medium red; opens: same general color or lighter shade (with coral undertone). Size — small.

Bloom:

*Size when fully open.*—Small, averaging about 35 to 38 mm (1½"). Petalage — double 22–26 petals, arranged regularly. Form — full; high center at first, becoming more open in the center, with petals rolled loosely outward, and later at maturity open, with petals slightly folded downward at edges and rolled loosely outward and downward. Open flowers show yellow stamens.

Petals: Thick; satiny on inside and on outside surface.

*Shape.*—Outside petals, broad lanceolate with rounded tip; intermediate — broad lanceolate with rounded tip; inside — lanceolate with rounded or small acute tip.

Color: Newly opened flower from a plant grown in plastic greenhouse (March, 1976), Visalia, Calif.

*Outside petal.*—Outside surface — near Geranium Lake 20/2 with both lighter and darker areas, and with small near white area at base; inside surface — similar to Geranium Lake 20/2 or lighter, shading into near white at base.

*Intermediate petal.*—Outside surface — similar to outside petal. Inside surface — similar to outside petal.

*Inner petal.*—Outside surface — same as intermediate petal; inside surface — same as intermediate petal. General color effect newly opened flowers — bright pink to deep pink but with an orange or coral tone. Three days open — color similar to newly opened flowers but petal tips on upper surface have become deeper shade. Behavior — as flowers age the inside (upper) surface of petals (area exposed to sunlight) tend to deepen in color — often becoming quite red. Spent petals drop off. Flower longevity (October 1976) — plant in pot 5–7 days or longer. Cut flowers at living room temperature 4–7 days.

Reproductive organs:

*Stamens.*—Abundant, arranged regularly about pistil.

*Filaments.*—Varying length, light yellow, medium length.

*Anthers.*—Well formed; yellow.

*Anthers.*—Well formed; yellow.

*Pollen.*—Fair amount.

*Pistils.*—Average number.

*Styles.*—Fairly even; short to medium length; bunched; color — near white to yellowish.

*Stigma.*—Nearly white.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; abundant; medium small; leathery; glossy.

*Leaflets.*—Shape; broad lanceolate, nearly oval; apex acute; base rounded or rounded acute. Margin serrate. Color: medium green; new growth — reddish. Rachis: medium strength; upper side may have few tiny short prickles, grooved; underside sparsely to moderately thorny with few or no tiny prickles. Stipules: short to medium long; medium width, medium length narrow points which turn out usually at about 45° or less.

Growth:

*Habit.*—Dwarf; bushy; upright; much branched.

*Growth.*—Free vigorous.

*Canes.*—Medium; slender; sturdy.

*Main stems.*—Color: medium to deep green.

*Thorns.*—Average number — (7 per 10 cm of main stems) — Fairly large, nearly straight, inclined slightly downward; color: brown — on older wood thorns may become gray. Prickles — none. Hairs — none.

*Branches.*—Color: medium green. Thorns: average; medium length; slender; nearly straight; inclined slightly downward. Color: brown. Medium to short oval base. Prickles: none. Hairs: none.

*New shoots.*—Color: reddish. Thorns: average; color: reddish; straight. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, essentially as illustrated and described, characterized by buds and flowers of a coral pink to light red color resembling the Persian Princess miniature rose (U.S. Plant Pat. No. 3,181) but often being somewhat more pink in the bud and opening stages, then becoming more red in the maturing and final stages (especially when grown outdoors), the form and size of bud and flower also being similar to Persian Princess; and further characterized by a plant which is vigorous and relatively compact, said plant being easy to propagate from cuttings, with small, disease resistant, glossy foliage, an abundance of bloom with excellent keeping quality, with flowers borne singly or several to the stem in loose clusters.

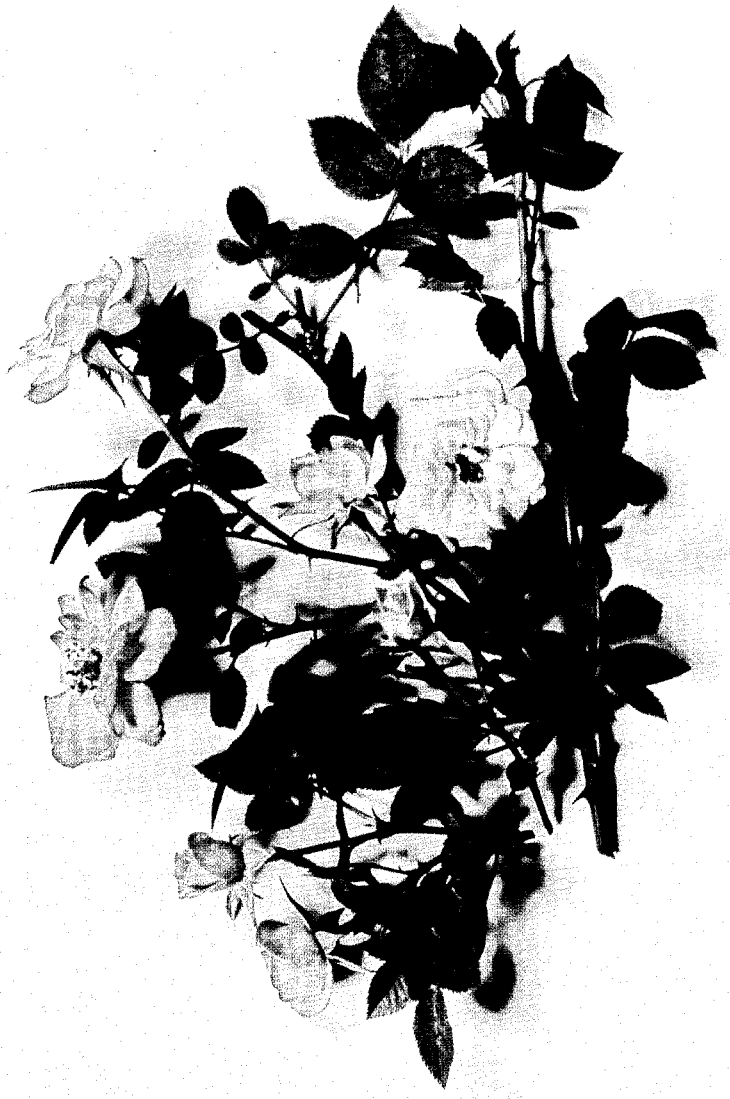

* * * * *